(12) United States Patent
U'ren

(10) Patent No.: US 6,280,945 B1
(45) Date of Patent: Aug. 28, 2001

(54) UNIVERSAL SOLID-PHASE HYBRIDIZATION APPARATUS

(75) Inventor: Jack U'ren, Kirkland, WA (US)

(73) Assignee: Saigene Corporation, Seattle, WA (US)

( * ) Notice: Subject to any disclaimer, the term of this patent is extended or adjusted under 35 U.S.C. 154(b) by 0 days.

(21) Appl. No.: 09/367,796

(22) PCT Filed: Feb. 19, 1997

(86) PCT No.: PCT/US98/03085

§ 371 Date: Jan. 6, 2000

§ 102(e) Date: Jan. 6, 2000

(87) PCT Pub. No.: WO98/37236

PCT Pub. Date: Aug. 27, 1998

Related U.S. Application Data

(60) Provisional application No. 60/037,426, filed on Feb. 21, 1997.

(51) Int. Cl.[7] .............................. C12Q 1/68; C12P 19/34
(52) U.S. Cl. .............................................. 435/6; 435/91.2
(58) Field of Search ........................................ 435/6, 91.2

(56) References Cited

U.S. PATENT DOCUMENTS 5,516,635  5/1996  Ekins et al. ............................... 435/6

OTHER PUBLICATIONS

Heerman et al. J. Virol. Meth. 59 (1–2)33–43, 1996.*

Managiapan, G., et al., "Sequence Capture–PCR Improves Detection of Mycobacterial DNA in Clinical Specimens," *J. of Clin. Microbiol.*, 34(3):1209–1215 (May 1996).

Urdea et al., "A comparison of non–radioisotopic hybridization assay methods using fluorescent chemiluminescent and enzyme labeled synthetic oligodeoxyribonucleotide probes," *Nucleic Acids Research*, 16(11):4937–4956 (1989).

Engvall, E., "Enzyme Immunoassay ELISA and EMIT," *Methods in Enzymology*, 70:419–439 (1980).

Holodniy, M., et al., "Detection and Quantification of Gene Amplification Products by Nonisotopic Automated System," Biotechniques, Jan. 12 (1):36, 38–39 (1992).

* cited by examiner

Primary Examiner—Eggerton A. Campbell
(74) Attorney, Agent, or Firm—Townsend and Townsend and Crew LLP

(57) ABSTRACT

A method of determining the presence of a nucleic acid analyte from a sample comprising binding a biotinylated capture oligonucleotide to a solid phase non-covalently coated with streptavidin or an avidin derivative. The capture oligonucleotide is contacted with and selectively hybridized to, under stringent hybridization conditions, a nucleic acid analyte to form a detectable hybridization complex.

11 Claims, No Drawings

UNIVERSAL SOLID-PHASE HYBRIDIZATION APPARATUS

CROSS REFERENCE TO RELATED APPLICATION

This application is a continuation-in-part of U.S. provisional application U.S. Ser. No. 60/037,426 (U'ren), filed Feb. 21, 1997.

FIELD OF THE INVENTION

The present invention relates to a method of solid phase hybridization in which streptavidin or derivatives thereof are non-covalently coated on the solid phase. Streptavidin and its derivatives prove stable under high temperature, high stringency hybridization conditions.

BACKGROUND OF THE INVENTION

Nucleic acid based diagnostics is enjoying particularly rapid growth at a time which has seen the overall demand for diagnostic assays continue to rise. Undoubtedly, this growth has been hastened by the increased pressure on medical professionals to contain costs. In response, the medical establishment is placing a growing emphasis on early intervention and prevention. Accordingly, assays which alert clinicians to a disease susceptibility have engendered strong interest. Nucleic acid based diagnostic assays promise to play a leading role in the expanding market for diagnostic assays.

Perhaps the single most critical step in nucleic acid based diagnostic assays is the selective hybridization of an oligonucleotide to its complementary target. A particularly favored means of accomplishing this has been through the use of solid phase supports. Solid phase DNA probe hybridization typically involves the direct or indirect covalent attachment of a synthetic "capture" oligonucleotide to a solid phase. The capture oligonucleotide is brought in contact with a sample comprising DNA or RNA under stringent hybridization conditions to promote duplex formation between the capture oligonucleotide and a complementary nucleic acid in the sample. Covalent attachment procedures require multiple chemical steps (which effect yield) and special handling equipment for the solid phase. Thus, it is costly and troublesome to change the particular oligonucleotide attached to the solid support. Previously, the severity of these problems was partially overshadowed by the relatively high cost and labor-intensive assay formats then in use. Today, however, the high capacity, high throughput, automated assay systems demanded by clinical laboratories has drawn increasing attention to the issues of manufacturing cost and complexity.

Application WO 90/10717 describe an attempted solution to the problem. In that publication, a nucleic acid tail of known sequence is attached to a capture oligonucleotide and the complement to the tail portion is covalently attached to the solid phase. Each new capture oligonucleotide shares the same tail such that the same solid phase can be used for all products. However, this approach requires that the tail oligo-complement hybrid be stable under the conditions of the sample hybridization. Since the sample hybridization conditions may vary with each new sample target, this approach requires a long region of complementarity to accommodate the high melting temperatures of possible target-oligonucleotide hybrids. Unfortunately, these long oligonucleotides have an increased risk of binding to non-target nucleic acids. Moreover, the secondary structural characteristics of long single strand nucleic acids can hinder access to the target.

Holodniy et al. (*Biotechniques*, 12:36–39 (1992)) describe the detection and quantification of gene amplification products using a solid phase which is non-covalently coated with avidin. However, in that system hybridization is accomplished at 42° C., a hybridization temperature often too moderate for high stringency hybridization.

Accordingly, what is needed in the art is a solid-phase hybridization apparatus which is tolerant of high-temperature and high stringency hybridization conditions and which can be readily, quickly, and inexpensively adapted to detect a variety of nucleic acid targets. The present invention provides these and other advantages.

SUMMARY OF THE INVENTION

In one aspect the present invention relates to a method of determining the presence or absence of a nucleic acid analyte from a sample. The method comprises the steps of binding a biotinylated capture oligonucleotide to the solid phase which is non-covalently coated with streptavidin or an avidin derivative. Simultaneous with, prior to, or subsequent to the binding step, the capture oligonucleotide is contacted with the nucleic acid analyte under stringent hybridization conditions with a temperature of at least 50° C. Under stringent hybridization conditions the capture oligonucleotide selectively hybridizes with the analyte to form a hybridization complex. The complex is detected as an indication of the presence or absence of said analyte in said sample.

In one embodiment, the solid phase is coated with avidin or streptavidin. In another embodiment, binding of the capture oligo and contacting the capture with the nucleic acid analyte are performed simultaneously. In a preferred embodiment, the solid phase is polystyrene. Preferably, the capture oligonucleotide is bound to the solid phase by a spacer of at least 36 covalent bonds in length. In another embodiment, stringent hybridization conditions are performed at between 55° C. and 70° C., or with a hybridization buffer having a chaotrope concentration of at least 1 molar. Preferably, the chaotrope is guanidine thiocyante. In another embodiment, the hybridization complex is detected by way of labelled primers used for nucleic acid analyte amplification.

In another aspect, the present invention is directed to a method of determining the presence or absence of a nucleic acid analyte from a sample. The method comprises the steps of binding a biotinylated capture oligonucleotide to the solid phase which is non-covalently coated with streptavidin or an avidin derivative. Simultaneous with, prior to, or subsequent to the binding step, the capture oligonucleotide is contacted with the nucleic acid analyte under stringent hybridization conditions with a temperature of at least 25° C. and a chaotrope concentration of at least 1 molar. Under stringent hybridization conditions the capture oligonucleotide selectively hybridizes with the analyte to form a hybridization complex. The complex is detected as an indication of the presence or absence of said analyte in said sample. In some embodiments the chaotrope is guanidine thiocyanate. In other embodiments the temperature is at least 40°. In additional embodiments the chaotrope concentration is at least 2M. The present invention has utility as an inexpensive, uncomplicated solid phase assay which can be rapidly adapted to detect a wide variety nucleic acid analytes.

DETAILED DESCRIPTION OF THE INVENTION

The present invention is directed to compositions and methods for determining the presence or absence of a nucleic acid analyte from a sample. Generally, the method comprises binding a biotinylated capture oligonucleotide to a solid phase non-covalently coated with streptavidin or an avidin derivative. The capture oligonucleotide is contacted with, and specifically hybridizes under stringent conditions to, a nucleic acid analyte to form a hybridization complex. The presence or absence of the hybridization complex is an indication of the presence or absence, respectively, of the nucleic acid analyte in the sample. The steps for binding, and formation of the hybridization complex can be carried out sequentially in any order, or simultaneously per the desired assay format.

Quite surprisingly, we have determined that streptavidin and avidin derivatives unexpectedly remain non-covalently bound to each other and to a hydrophobic solid support under the harsh conditions of high temperature and/or high concentrations of chaotrope. Accordingly, the present invention provides solid phase supports which obviate the requirement for covalent attachment of oligonucleotides or streptavidin to the support. In turn, the costs and complications attendant with covalent attachment are eliminated.

Definitions

Unless defined otherwise herein, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York), and Hale and Marham (1991) *The Harper Collins Dictionary of Biology*, Harper Perennial, N.Y. provide one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

As used herein, "nucleic acid analyte" refers to a nucleic acid whose absence or presence in a sample is to be determined. The term "nucleic acid" refers to a deoxyribonucleotide or ribonucleotide polymer in either single- or double-stranded form, and unless otherwise limited, encompasses known analogs of natural nucleotides that hybridize to nucleic acids in manner similar to naturally occurring nucleotides.

As used herein "label" or "labeled" refers to a composition which is detectable by spectroscopic, photochemical, biochemical, immunochemical, electromagnetic, radiochemical, or chemical means such as fluorescence, chemifluoresence, or chemiluminescence. For example, useful labels include 32P, fluorescent dyes, electron-dense reagents, enzymes (e.g., as commonly used in an ELISA), biotin, dioxigenin, or haptens and proteins for which polyclonal or monoclonal antibodies are available.

A "labeled nucleic acid probe" is a nucleic acid probe that is bound, either covalently or through ionic, van der Waals or hydrogen bonds, directly or through a linker, to a label such that the presence of the probe may be detected by detecting the presence of the label bound to the probe.

As used herein "stringent hybridization conditions" are generally selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular probe. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, N.Y.

As used herein "sample" refers to a specimen having or suspected of having a nucleic acid analyte. The term includes biological, soil, aquatic and air specimens.

As used herein, "biological sample" refers to any sample obtained from a living organism or from an organism that has died. Examples of biological samples include body fluids and tissue specimens including cell lysates.

As used herein "binding" "bind" or "bound" means the formation of a high affinity non-covalent bond between biotin or a derivative thereof and streptavidin or an avidin derivative. Typically, such bonds have dissociation constants of about $10^{-15}$M.

As used herein, "biotinylated" means modification with biotin or a biotin derivative. A biotin derivative will form a non-covalent high affinity bond with streptavidin or an avidin derivative such that at least 75% of such bonds are intact per unit of time under stringent hybridization conditions.

As used herein, "oligonucleotide" or "oligo" means a nucleic acid of at least 12 nucleotides or nucleotide analogs in length, preferably at least 20 nucleotides in length.

As used herein, "capture oligo" or "capture oligonucleotide" refers to an oligonucleotide labelled internally or at the 3' or 5' terminal ends or any combination thereof, with biotin or a derivative thereof. The capture oligonucleotide comprises a sequence which selectively hybridizes, under stringent hybridization conditions, to a sequence present in the nucleic acid analyte.

As used herein, "non-covalently coated" or "coated" means adsorbed onto a surface by any non-covalent bond such as ionic, hydrophobic, van der Waals, or hydrogen such that at least 75%, preferably at least 80% and most preferably at least 85% of such bonds remain intact per unit of time under stringent conditions.

As used herein, a "avidin derivative" refers to avidin and structurally related compounds (i.e., analogs) which can be non-covalently coated onto the solid phase of the assay apparatus employed. Streptavidin and its avidin derivatives are collectively referred to as "coating agents."

As used herein, "contacting" means to bring in direct physical association.

As used herein "detecting" means to quantitatively or qualitatively determine the extent or degree of.

As used herein, "chaotrope" means a chemical composition which acts to disrupt the duplex structure of nucleic acids. Chaotropes are frequently used in reactions to lower the $T_m$ of nucleic acid duplexes.

As used herein, "selectively hybridize" or "selectively hybridizes" means to hybridize to nucleic acids which are substantially identical. An indication that two nucleic acid sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

As used herein, "solid phase" means a solid surface onto which streptavidin or an avidin derivative is bound.

As used herein, "target nucleic acid" means the nucleic acid to which selective hybridization by the capture oligonucleotide is desired.

As used herein, "covalent bonds in length" refers to the smallest number of covalent bonds covalently linking two referenced compounds.

Typical chaotropes include LITCA, GuSCN, NaSCN, NaClO$_4$; Kl, GuCl, CsTFA. Chaotropes are also described in Nucl. Acids Research Vol. 19 (19) 5146 which is incorporated herein by reference.

I. The Solid Phase

The solid phase of the present invention is selected from any number of hydrophobic supports which can be non-covalently coated with streptavidin or avidin derivatives (collectively, "coating agents"). Suitable hydrophobic polymers for use as a solid phase include, but are not limited to, polystyrene, polypropylene, polyethylene, polyvinyl chloride, and combinations or derivatives thereof. Preferably, the solid phase is polystyrene; however, nitrocellulose may also be employed. Any number of other solid phase materials can be readily determined using coating agents which remain bound to the solid phase under the desired stringent conditions. Thus, for example, the percentage of labelled streptavidin which, after coating, remains bound to the solid phase under stringent conditions per a given time period will determine the appropriateness of that particular solid phase.

II. Coating Agents

In a preferred embodiment, the coating agent will be streptavidin. However, avidin and avidin derivatives such as NEUTRA-AVIDIN (Pierce Chemical Co., Rockford, Ill.) can be used. Streptavidin and avidin derivatives are proteins that, as those of skill in the art will appreciate, can be derivatized via substitution, deletion or addition of amino acid residues while retaining the high affinity non-covalent interaction typical of that associated with the streptavidin and biotin. Streptavidin or its avidin derivatives can also be chemically modified. For example, the terminal amino or carboxyl groups can be modified to afford greater resistance to proteolytic enzymes, or bifunctional linkers may be used to form dimers of the coating agents. The efficacy of various avidin derivatives can be readily be assessed by assaying for their ability to coat the solid phase. For example, avidin derivatives can be radiolabelled and the percentage of label remaining under stringent hybridization conditions per unit time will determine their efficacy as coating agents.

III. Coating the Solid Phase

The solid phase is coated with a coating agent by immersing, spraying, or otherwise saturating the region of the solid phase which is to be coated with a solution comprising the desired coating agent(s). Typically, the coating agent is solubilized in an alkaline buffer such as a phosphate or bicarbonate buffer. The concentration of coating agent in solution will vary according to the surface area to be coated and the volume of solution used. Typically, however, the concentration of coating agent ranges from 1 to 10 $\mu$g/ml in buffer.

The length of time required to achieve the desired degree of coating will vary with the concentration of coating agent and the temperature at which the coating step is performed. Coating is conveniently accomplished at temperatures ranging from 4° C. to room temperature. However, coating temperatures ranging from above freezing to 70° C. may be employed. Thus, for example, coating and selective hybridization between the capture oligo and the nucleic acid analyte may be performed simultaneously under stringent hybridization conditions.

The efficiency of coating can be readily assessed by, for example, performing a titration curve with a coated solid phase of known surface volume using labelled biotin. In a preferred embodiment, coating is rapidly and efficiently achieved in 5 minutes at 30° C. by immersion of the solid phase in a solution of 10 $\mu$pg streptavidin per ml of 0.1 M phosphate buffer, pH 8.0. Wash steps are typically employed subsequent to coating to remove unbound coating agent.

IV. Oligonucleotides

Nucleic acid hybridization is based upon the pairing of complementary nucleic acid strands. When complementary single stranded nucleic acids are incubated in appropriate buffer solutions and conditions, complementary nucleotide sequences pair to form stable, double stranded molecules (i.e., the sequences hybridize to form a hybridization complex or duplex). The particular technique employed is not essential to the method of the present invention, and one of ordinary skill in the art will appreciate the variety of such techniques. See, e.g., Hames, et al. (eds.), "Nucleic Acid, A Practical Approach", IRL Press, New York, 1985. As improvements are made in techniques, they will be readily applicable to the present invention.

As those of skill in the art will readily understand, the capture oligonucleotide need not be perfectly complementary to the target nucleic acid. For example, a non-complementary nucleotide sequence may be attached to an otherwise complementary capture oligo or, alternatively, non-mismatched bases can be interspersed into the otherwise complementary capture oligo sequence, provided that the capture oligo as a whole has sufficient complementarity with the sequence of the target nucleic acid to hybridize selectively with the target to form a hybridization complex. The degree of complementarity will optimally be 100 percent; however, minor mismatches can be accommodated by reducing the stringency of the hybridization solution and/or wash solution. It will be understood by those of skill that by varying the temperature, salt concentration, etc., stable hybrids can be formed even in the presence of mismatches. Thus, despite the lack of 100 percent complementarity, functional probes having minor base differences from their target nucleic acid sequences are possible under reduced conditions of stringency Under conditions of reduced stringency, therefore, it may be possible to modify up to 60% of a given oligonucleotide probe while maintaining an acceptable degree of specificity. However, the degree of acceptable mismatching is dependent upon the specificity required, in a manner recognized by a practitioner in the art. In addition, analogs of nucleosides may be substituted within the probe for naturally occurring nucleosides.

Nucleic acid hybridization generally entails controlling the stability of hydrogen and hydrophobic bonds leading to duplex formation. To this end, chaotropic agents and temperature are frequently varied. Chaotropic agents include guanidine thiocyanate, lithium trichloroacetic acid, sodium isothiocyanate, sodium perchlorate, and sodium iodide. Stringent hybridization conditions typically require a temperature of T degrees °C., where T is any integer selected from the group consisting of the integers from 20 to 70, inclusive, more typically between 25 to 65, and preferably 30 to 60, depending upon the concentration of chaotropic agent and the melting temperature and degree of complementarity between the hybridizing oligos. Preferably, the temperature of hybridization is at least 50° C. without the use of chaotrope; and at least 25° C., preferably at least 30° C., 35° C., or 40° C. with chaotrope. Chaotropes are typically employed at concentrations ranging from each of the values from 1.0 to 4.0 molar. Hybridization times range from each 0.1 hour increment from 0.1 hour to 24 hours.

The length and sequence of the biotinylated capture oligo will be chosen to accommodate the assay format, its conditions, and the degree of selectivity desired. Oligos are typically range from each of the values between 20 to about 100 nucleotides in length, but may be as long as about 200, 300, 400, or 500. Oligos may be synthesized or cloned according to methods well known to those of skill in the art. For example, the solid phase phosphoramidite method can be used to produce short probes of between 6 and 100 bases having a molecular weight of less than 16,000 daltons. See, Caruthers, et al., *Cold Spring Harbour Symp. Quant. Biol.* 47:411–18, 1982; and Adams, et al., *J. Am. Chem. Soc.* 105:661, 1983, for the synthesis of oligonucleotides.

V. Binding a Biotinylated Capture Oligo to the Coating Agent

One or more species of biotinylated capture oligonucleotide are bound to the solid phase under reaction conditions that foster the non-covalent, high-affinity bonds between biotin and streptavidin or its avidin derivatives. Such conditions are well known to those of skill in the art. See, e.g., Methods in Enzymology 184:537–541 (1990), Vann et al., Ed. M. Wilchek et al., Academic Press, San Diego, Calif. Further, the present invention provides that these high affinity bonds can be formed and sustained under stringent hybridization conditions.

Biotinylation of the capture oligonucleotide may be effected by any number of means well known to those of skill in the art, such as through nick translation. Typically, however, biotinylated oligonucleotides are synthesized using a biotinylated 5' terminal monomer widely available through commercial sources (e.g., Glen Research, Sterling, Va.). Preferably, the oligonucleotide is biotinylated at the 5' terminus. Even more preferably, the biotin moiety is linked to the oligonucleotide by a polar spacer of at least 18 covalent bonds in length such as via a spacer comprising repeating ethoxyl groups, most preferably by at least 36 covalent bonds in length.

VI. Biotinylated Capture Oligo

Prior to, during, or subsequent to binding, the biotinylated capture oligonucleotide is placed in physical contact with the nucleic acid analyte under stringent conditions. Hybridization conditions can be adjusted to allow for selective hybridization between only perfectly complementary oligonucleotides, or with oligos having 1, 2, 3, 4, 5, or more mismatches.

Typically, following binding of the biotinylated oligo to the solid phase, and after the hybridization step, a washing step is employed to remove unbound material which may interfere in subsequent steps or in detection. The wash solution is not a critical aspect of the present invention and may be selected from any number of wash buffers well known to those of skill in the art. The stringency of the washes may be varied to be greater, lesser, or of equivalent stringency to the hybridization stringency according to the degree of selectivity desired. Any of a number of hybridization wash solutions known in the art may be suitably employed herein. See, e.g., Berger and Kimmel, Guide to Molecular Cloning Techniques, Methods in Enzymology volume 152 Academic Press, Inc., San Diego, Calif. (Berger); Sambrook et al. (1989) Molecular Cloning—A Laboratory Manual (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel).

VII. Detection

After allowing for formation of the hybridization complex, the presence or absence of the complex is detected as an indication of the presence or absence of the nucleic acid analyte in the sample. The method of detecting the presence or absence of the hybridization complex is not a critical aspect of the invention. Generally, however, the presence of the hybridization complex is determined by the presence of a nucleic acid analyte specific probe which is linked, via the intermediate and biotinylated oligos, to the solid support. Accordingly, signal oligonucleotide probes which selectively hybridize, under stringent hybridization conditions, to the nucleic acid analyte are useful in accordance with the methods of the present invention. Preferably, however, the nucleic acid analyte is itself labelled during an amplification stage. Thus, for example, labelled PCR primers may be used to detect the presence of the hybridization complex. Examples of other amplification systems include the ligase chain reaction (LCR), the nucleic acid sequence based amplification (NASBA, Cangene, Mississauga, Ontario) and Q-Beta Replicase systems. When such amplification methods are used to enhance the sensitivity of the assay, the amplicon of the target nucleic acid is subsequently detected in the assay.

Generally, labelled oligos or primers are conjugated to or conjugable with detectable labels. Detectability may be provided by such characteristics as enzymatic activity, color change, luminescence, fluorescence, or radioactivity, or it may be provided by the ability of the reporter group to serve as a ligand recognition site. Any haptenic or antigenic compound can be used in combination with a suitably labelled antibody for this purpose.

Exemplary enzymes of interest as reporter groups are hydrolases and, in particular, phosphatases, esterases, ureases, and glycosidases, oxidoreductases, particularly peroxidases, and the like. Fluorescent compounds include fluorescein and its derivatives, rhodamine and its derivatives, dansyl, umbelliferone, and the like. Chemiluminescers include luciferin, luminol, oxetane-diones, and the like. The above list is illustrative only, and the choice of label depends on sensitivity requirements, ease of conjugation with the probe, stability requirements, and available instrumentation.

Although the present invention has been described in some detail by way of illustration and example for purposes of clarity of understanding, it will be obvious that certain changes and modifications may be practiced within the scope of the appended claims.

EXAMPLE 1

Example 1 describes the coating of the solid support with streptavidin.

Beaded lids ("prong strips") (Falcon, Cat. No. 3931, Lincoln Park, N.J.) were coated with 10 μg/ml streptavidin (Boehringer Mannheim, Indianapolis, Ind. Cat. No. 1,097, 679) in 0.1 M $Na_2HPO_4$ buffer pH 8.0 in a 96 well vinyl microwell plate at 4° C. overnight. The beaded lid was washed 2 times with phosphate buffered saline (PBS) for 5 min each, blocked with 1% bovine serum albumin in PBS for 2 hr at room temperature, washed 2 times with PBS for 5 min each, washed 2 times with PBS containing 0.5% Tween 20 for 5 min each, washed 2 times with 10 mM Tris, 1 mM EDTA, 0.1% Na azide, pH 7.5 for 5 min each, air dried, and stored in a desiccator.

The uniformity and batch reproducibility of the streptavidin coated prongs were assayed by incubating the prongs in 12.5 nanogram/ml biotinamidocapryl-horse radish peroxidase (HRP) (Sigma Cat. No. P 9568) for 5 min. The prongs were washed twice with 0.1 M NaCl, 0.05 M Tris, 0.5% CTAB (cetyltrimethylammonium bromide), pH 8.0 for 1 min each and assayed for the amount of HRP bound in TMB (3,3',5,5' tetramethylbenzidine) enzyme-immunoassay (EIA) substrate (BioRad, Hercules, Calif. Cat. No. 172-1068) for 8 min. With a strip of 12 prongs the average color development at 650 nm was 1.516 with a coefficient of variation (CV) of 4.3%. Batch to batch variation was greater but on average was about 10%.

EXAMPLE 2

Example 2 demonstrates the improved results using a spacer on the capture oligonucleotide.

When the streptavidin coated prongs are used in an assay to bind a biotinylated capture oligo followed by hybridization to a target DNA, the results varied greatly depending on the size of the target molecule. If a synthetic oligo of 18 nucleotides in length and complementary to the capture oligo was used as a target, the assay generated the expected color reaction as quantitated by the microwell assay of Example 3. However, if the target was a PCR product of the HLA DQβ allele 0302 of 131 nucleotides in length, very little color was generated. Compositions and methods for detection of HLA DQβ1 alleles is described in a commonly assigned patent application Ser. No. 09/367,905 filed Feb. 21, 1997 the teachings of which are incorporated by reference herein.

To explore whether steric hinderance of the much larger PCR product caused the poor results, we added 18 atom spacer arms between the 5' end of the oligo and the biotin TEG phosphoramidite (which already had a 21 atom spacer between the terminal phosphate and the biotin moiety). One, two, and three additional spacers were examined. Table I shows the results. While all versions of the capture oligos efficiently captured the synthetic target, only the spacer modified capture oligo would capture the PCR product, with two spacers being optimal.

TABLE I

| # OF ADDED SPACERS | NO TARGET | SYNTHETIC OLIGO TARGET | 0302 PCR PRODUCT |
| --- | --- | --- | --- |
| None | 0.046 | 1.715 | 0.049 |
| One | 0.050 | 1.946 | 0.373 |
| Two | 0.045 | 1.614 | 0.693 |
| Three | 0.041 | 2.419 | 0.375 |

EXAMPLE 3

Example 3 describes comparison of the universal solid phase assay format with a standard dipstick assay using PCR amplified regions of the human leukocyte antigen (HLA) alleles, DQB1 0201, 0302, and 0602.

For the dipstick assay, a dipstick containing press fit nylon beads which have allele specific and control oligos attached is placed in well 2 of an eight tube microtube cassette. Ninety microliters of a neutralizing reagent (1 M NaH$_2$PO$_4$, pH 4.0) is added to well 1. The dipstick is moved from well 2 through the eight wells of reagents (Table II) in a time controlled manner. Upon completion of the assay, any blue color on the beads indicate whether an allele was present or not.

The well components, their volumes and the program steps and times are indicated in Table II:

TABLE II

| WELL # | CONTENTS | VOLUME μl | PRGM. STEP | TIME min. |
| --- | --- | --- | --- | --- |
| 1 | 60 mM NaOH | 815 | 1 | 10 |
| 2 | 0.1 M Na$_2$HPO$_4$, pH 7.24 | 900 | 2 | 2 |
| 3 | 0.1 M Na$_2$HPO$_4$, pH 7.24 | 900 | 3 | 1 |
| 4 | 0.1 M Na$_2$HPO$_4$, pH 7.24 | 900 | 4 | 1 |
| 5 | streptavidin-peroxidase conjugate | 900 | 5 | 5 |
| 6 | Wash buffer* | 900 | 6 | 3 |
| 7 | Wash buffer* | 900 | 7 | 2 |
| 8 | TMB-ELISA | 900 | 8 | 10 |

*Wash buffer is 10 mM Tris, 1 mM EDTA, 91 mM NaCl, 35 mM SDS, and 34 mM N-Lauryl Sarkosyl, pH 8.0. The PCR products were labeled by using a primer with a 5'-fluorescein moiety.

In the universal solid phase assay format, capture probes were employed which specifically hybridized with the PCR products and were 5' biotinylated via two contiguous 18 atom spacers. The solid phase was a polystyrene dipstick which was coated with streptavidin as in Example 1. A cassette was employed that consisted of a microwell strip filled with the following reagents (Table III) through which the dipstick was moved in the programmed steps and times as indicated:

TABLE III

| WELL # | VOLUME ul | WELL CONTENTS | PRGM. STEP | TIME MIN. |
| --- | --- | --- | --- | --- |
| 1 | | EMPTY | 3 | 10 |
| 2 | 150 | 2.6 M GuSCN, 17 mM EDTA, 1.76 M FORMAMIDE, 83 mM TRIS, pH 7.5 | 2 | 2 |
| 3 | 150 | CAPTURE PROBES IN 0.1 M Na$_2$HPO$_4$ 0.5% TWEEN-20, pH 7.2 | 1 | 10 |
| 4 | 150 | ANTI-FLUORESCEIN-PEROXIDASE CONJUGATE | 5 | 5 |
| 5 | 200 | 0.1 M Na$_2$HPO$_4$, 0.5% TWEEN-20, pH 7.2 | 4, 6 | 1, 1 |
| 6 | 200 | 0.1 M NaCl, 0.05 M TRIS, 0.5% CTAB, pH 8.0 | 7 | 1 |
| 7 | 200 | 0.1 M NaCl, 0.05 M TRIS, 0.5% CTAB, pH 8.0 | 8 | 1 |
| 8 | 150 | TMB EIA | 9 | 8 |

The assay was performed at 30° C. Ten μl of sample was added to 0.5 ml of the 2.6 M guanidine thiocyanate buffer and the tube was heated at 85° C. to denature the double stranded amplicon. The streptavidin coated dipstick was moved to well 3 where it binds the biotin labeled capture oligo. Next, the excess capture oligo and any loosely bound oligo was removed by a stringent wash in well 2. Twelve minutes from the assay start, 100 μl of the heated sample was added to well 1. The sample was added to each of four strips. Each strip has a capture oligo in well 3 which was specific for either the DQB1 0201/0202 alleles, the 0302/0303 alleles, the 0602 allele, or the DRA allele. The solid phase hybridized amplification product from well 1 was washed in well 5 and moved to the anti-fluorescein-peroxidase conjugate where it binds to any fluorescein labeled PCR primer present on the dipstick. The excess conjugate was washed off of the dipstick in wells 5–7 and the TMB substrate in well 8 turned from a clear solution to a blue solution if any peroxidase was carried via the dipstick into the well by binding to the amplification products. The plate containing the 8-well microwell strip can be quantitatively read at 650 nm using a microwell plate reader. The bead assay results were quantitated with a reflectance based reader since the dye precipitated on the beads. The results (Table IV) indicate that both formats perform equally well showing the expected sensitivity and specificity.

TABLE IV

HLA ALLELE DETECTION ASSAY FORMAT COMPARISON

| FORMAT SPECIFICITY | RATIO DQB/DRA | | | RATIO DQB/DRA | | |
|---|---|---|---|---|---|---|
| | MICROWELL 201 | MICROWELL 302 | MICROWELL 602 | BEAD 201 | BEAD 302 | BEAD 602 |
| 201 | 0.40 | −0.01 | 0.02 | 0.38 | 0.02 | 0.01 |
| 302 | 0.00 | 0.49 | −0.01 | 0.01 | 0.10 | 0.01 |
| 602 | 0.01 | 0.00 | 0.18 | 0.01 | 0.01 | 0.15 |

All publications and patents mentioned in this specification are herein incorporated by reference into the specification to the same extent as if each individual publication or patent was specifically and individually indicated to be incorporated herein by reference.

What is claimed is:

1. A low temperature method for determining the presence or absence of a nucleic acid analyte from a sample, said method comprising the steps:
   (a) binding a biotinylated capture oligonucleotide to said solid phase, wherein said solid phase is non-covalently coated with streptavidin or an avidin derivative;
   (b) contacting said capture oligonucleotide with said nucleic acid analyte under stringent hybridization conditions having a temperature of between 25° C. and 40° C. and a chaotrope concentration of at least 1 molar, wherein said capture oligonucleotide selectively hybridizes, under stringent conditions, with said analyte to form a hybridization complex; and
   (c) detecting the presence or absence of said hybridization complex as an indication of the presence or absence of said analyte in said sample.

2. The method of claim 1, wherein the capture oligonucleotide is bound to the solid phase by a spacer of at least 36 covalent bonds in length.

3. The method of claim 1 wherein the solid phase is coated with streptavidin.

4. The method of claim 1 wherein the binding step and the contacting step are performed simultaneously.

5. The method of claim 1 wherein the solid phase is polystyrene.

6. The method of claim 1 wherein the analyte nucleic acid is amplified with labeled primers.

7. The method of claim 1 wherein the streptavidin derivative is avidin or NEUTRA-AVIDIN.

8. The method of claim 1 wherein the sample is a biological sample.

9. The method of claim 1 wherein the chaotrope is guanidine thiocyanate.

10. The method of claim 1, wherein the chaotrope concentration is at least 2M.

11. The method of claim 1, wherein the temperature is between 25° and 30° C.

* * * * *